United States Patent
Nguyen et al.

(10) Patent No.: US 11,623,980 B1
(45) Date of Patent: Apr. 11, 2023

(54) HYBRID MYCELIAL CELLULOSE SHEET AND PREPARATION THEREOF

(71) Applicant: VU MON TECHNICAL AND TECHNOLOGY CO., LTD., Thuan An Town (VN)

(72) Inventors: Thuong Thi Lien Nguyen, Thuan An (VN); Chanh Minh Nguyen, Thu Dau Mot (VN)

(73) Assignee: VU MON TECHNICAL AND TECHNOLOGY CO., LTD., Thuan An Town (VN)

( * ) Notice: Subject to any disclaimer, the term of this patent is extended or adjusted under 35 U.S.C. 154(b) by 0 days.

(21) Appl. No.: 17/752,648

(22) Filed: May 24, 2022

(51) Int. Cl.
| | |
|---|---|
| C08L 1/04 | (2006.01) |
| C12N 1/14 | (2006.01) |
| C12P 19/04 | (2006.01) |
| C12P 1/02 | (2006.01) |
| C12P 39/00 | (2006.01) |
| C12N 1/20 | (2006.01) |
| C12N 1/04 | (2006.01) |
| C12P 1/04 | (2006.01) |
| A01G 18/20 | (2018.01) |
| C12N 1/22 | (2006.01) |
| C12R 1/645 | (2006.01) |
| C12R 1/02 | (2006.01) |

(52) U.S. Cl.
CPC .............. *C08L 1/04* (2013.01); *C12N 1/145* (2021.05); *C12N 1/205* (2021.05); *C12N 1/22* (2013.01); *C12P 1/02* (2013.01); *C12P 1/04* (2013.01); *C12P 19/04* (2013.01); *C12P 39/00* (2013.01); *A01G 18/20* (2018.02); *C12R 2001/02* (2021.05); *C12R 2001/645* (2021.05)

(58) Field of Classification Search
CPC .......... C12N 1/145; C12N 1/205; C12N 1/22; C12P 39/00; C12P 1/102; C12P 1/04; C12P 19/04; C08L 1/04; A01G 18/20; C12R 2001/645; C12R 2001/02
See application file for complete search history.

(56) References Cited

U.S. PATENT DOCUMENTS

2020/0392668 A1    12/2020    Ouzounov et al.

FOREIGN PATENT DOCUMENTS

IN    202111011043 A    6/2021

OTHER PUBLICATIONS

Attias (Year: 2020).*
Eichlerova (Year: 2005).*
Mohamed et al (Year: 2015).*
Elsacker (Year: 2021).*

* cited by examiner

Primary Examiner — Jeffrey S Lundgren
Assistant Examiner — Ibrahim D Bori
(74) Attorney, Agent, or Firm — Trojan Law Offices

(57) ABSTRACT

A leather-like hybrid mycelial cellulose sheet and production thereof. Precise selection of mushroom species and reagents allows for production at low pH, thereby resulting in a strong, flexible, and dry leather-like material suitable for application in various industries.

10 Claims, 2 Drawing Sheets

HYBRID MYCELIAL CELLULOSE SHEET AND PREPARATION THEREOF

BACKGROUND OF THE INVENTION

Leather sourced from cattle is widely used across industries including manufacturing, textiles, and fashion. This broad application creates significant demand for cattle, which creates environmental sustainability issues because leather production sourced from cattle requires significant investment in resources such as land, cattle feed, and time.

Due to the significant investment required for cattle leather, there exist alternative methods to create synthetic "leather-like" alternatives. However, such products are wrought with deficiencies. Drawbacks include expensive production, synthetic and environmentally unfriendly ingredients, and non-durable leather-like products.

Thus, A need exists for consistent, cost-effective and environmentally friendly methods for making durable, leather-like materials at a production scale capable of meeting the significant market demand.

SUMMARY OF THE INVENTION

The innovation herein relates to a method of production of synthetic, leather-like material comprising a hybrid of mycelium and bacterial cellulose. The product material is both durable and suitable for use in various applications.

The method comprises steps of providing a growth medium for the hybridization of mycelium and bacterial cellulose. Reagents include, but are not limited to, a source of carbohydrates (such as molasses), a fertilizer, (such as diammonium phosphate), a source of nitrogen (such as ammonium sulphate), an acid to make pH adjustments (such as acetic acid), a "building" material (such as calcium carbonate), a base to make pH adjustments (such as coconut water), and a reagent such as deionized water. The growth medium ingredients are mixed then sterilized. The growth medium is plated onto trays to which organic components are added to form the mycelium and bacterial cellulose. For example, cellulose producing bacteria, such as *Komagataeibacter xylinus* is added to the trays and then allowed to incubate. As they grow, the bacteria produce cellulose in a sheet-like layer. Fungi are then added to the sheet and another incubation period begins and mycelium is formed throughout the cellulose sheet. Generally, fungi cannot grow at the pH levels in which cellulose producing bacteria normally occupy, but the growth medium allows the fungi to proliferate.

The fungi combine with the cellulose produced by the bacteria forming a hybrid mushroom cellulose (HMC) sheet. After a growth phase the HMC sheet is removed from the trays and treated. Treatment includes a first and second processing, which includes exposure to boiling water then to warm sodium hydroxide. Then the HMC sheet is dried to yield a finished product—a synthetic leather-like material that is both strong and flexible and ready to be used in various industrial applications.

BRIEF DESCRIPTION OF THE DRAWINGS

These and other features and advantages of the present invention will become appreciated, as the same becomes better understood with reference to the specification, claims and drawings herein:

DETAILED DESCRIPTION OF THE INVENTION

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another element as illustrated in the Figures. It will be understood that relative terms are intended to encompass different orientations of the device in addition to the orientation depicted in the Figures.

Figure 1:
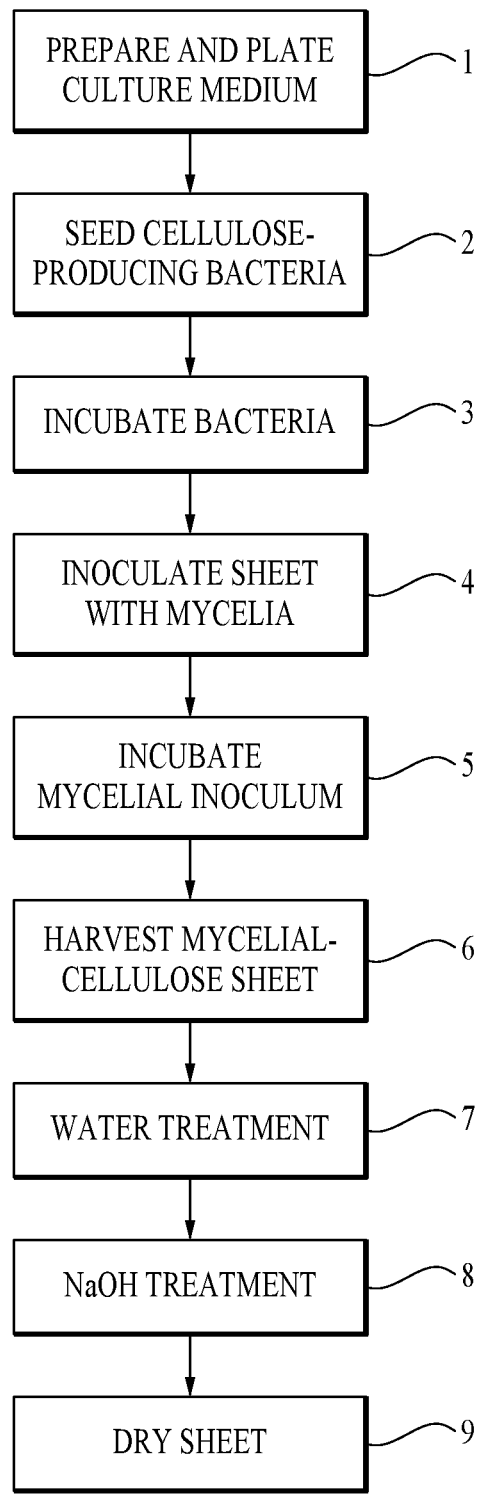
FIG. 1 shows a schematic for producing hybrid mycelial cellulose sheets.

As shown in FIG. 1 a growth medium 1 is prepared at atmospheric temperature and pressure. An embodiment of the growth medium comprises at least 1 L of water however media may be produced to any scaled volume. In an embodiment the reagents are comprised of molasses $C_6H_{12}NNaO_3S$, ammonium dihydrogen phosphate $(NH_4)H_2PO_4$, ammonium sulphate $(NH_4)H_2SO_4$, Acetic acid $CH_3COOH$, Water $H_2O$, and Calcium Carbonate $CaCO_3$. The molasses may be any household molasses.

The molasses concentration may be at least [5 g/L] up to [100 g/L] and preferably be [20 g/L]. Ammonium dihydrogen phosphate concentration may be at least [0.5 g/L] up to [5 g/L] and preferably be [2 g/L.] The ammonium sulphate may be at least [0.5 g/L] up to [10 g/L] and preferably be [8 g/L.] The calcium carbonate concentration may be at least [5 g/L] up to [30 g/L] and preferably [20 g/L.] The acetic acid may balance pH to at least 3.0 up to pH 5.5 and preferably achieve pH between 3.0 and 3.5. The reagents are mixed, and the growth media is heated. The media is heated to between 95° C. and 105° C., preferably 100° C. The heat may be applied for between 10 and 40 minutes, preferably 15 to 30 minutes. The media is placed in containers, preferably sterile containers and stored, preferably under sterile conditions.

Figure 2:
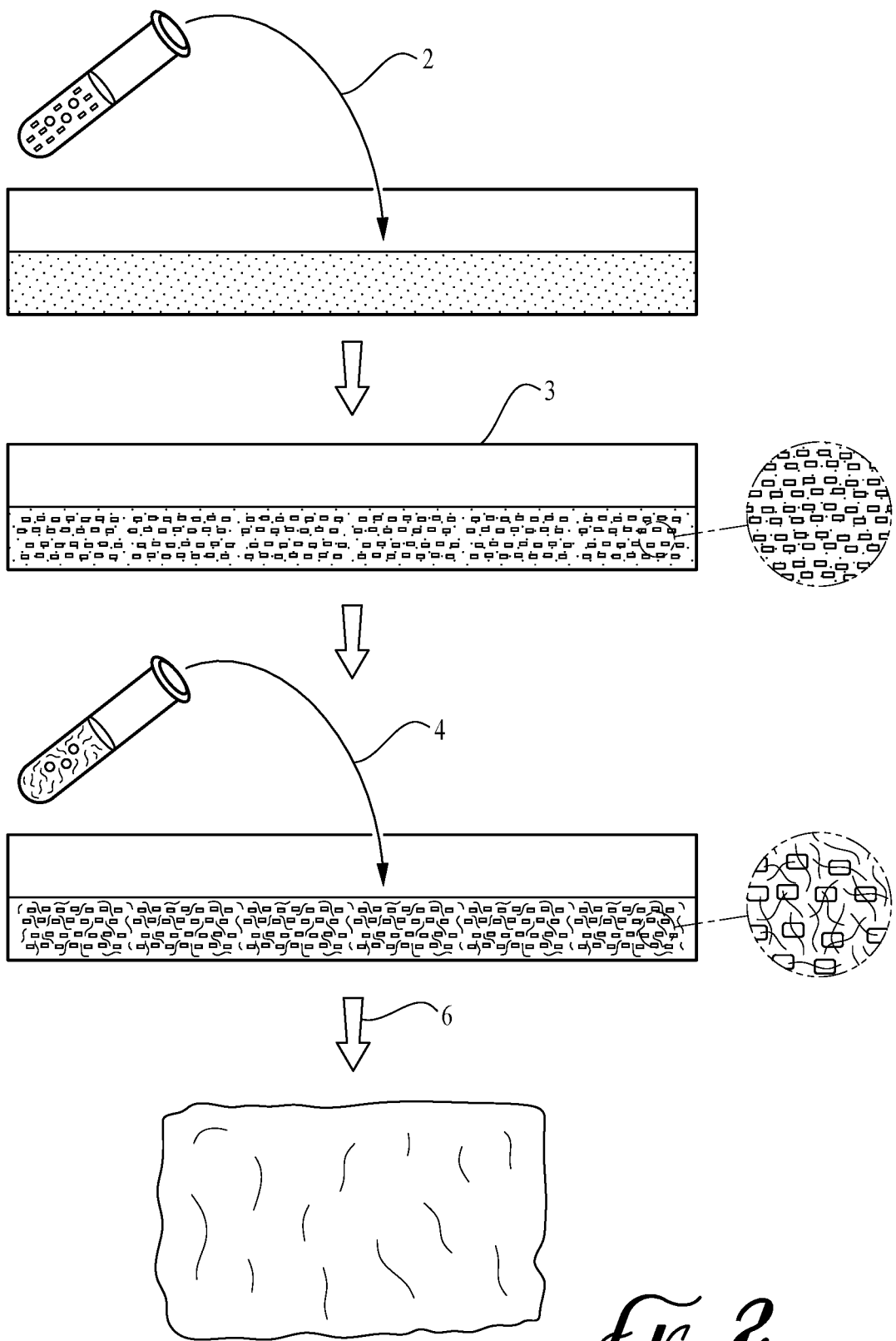
FIG. 2 depicts bacterial and mycelial steps as shown in FIG. 1 in greater detail.

As shown in FIGS. 1 and 2 the growth media is seeded 2 with cellulose producing bacteria, preferably *Komagataeibacter xylinus*. The bacterial amount administered may be 5% to 15% volume per volume of growth media, preferably 10%. Bacterial growth conditions may be under atmospheric conditions, preferably at 30-37° C. and 60-90% humidity. The bacteria produce cellulose while growing. Cellulose production during incubation 3 dictates mycelial growth medium inoculation with mycelia. In an embodiment, the cellulose layer may be of 1-40 mm thickness, and preferably of 10-20 mm. In another embodiment, mycelium is added after 9 days. Then, mycelium in solution is added to the cellulose sheet.

As shown in FIGS. 1 and 2 the cellulose sheet is inoculated 4 with a selection of mycelium that thrive at pH below 3.6, preferably *Ischnoderma resinosum*. The mycelium grows at a pH suitable to bacteria. A mycelium solution is prepared. The solution serves as a vehicle to inoculate the cellulose sheet with mycelium.

In an embodiment, the mycelium solution is comprised of the same ingredients used in the growth media. Like the growth media, the mycelial solution can be scaled to any amount of water, for producing HMC sheets in any amount. An embodiment for mycelial administration solution comprises 1 L water. The solution includes molasses, preferably [20 g/L]. The solution includes ammonium dihydrogen phosphate, preferably [2 g/L]. The solution includes ammonium sulphate, preferably [8 g/L]. The solution includes calcium carbonate, preferably [20 g/L]. Acetic acid may be used to balance the pH to a range including 3.0-3.5 pH.

The mycelia are placed in the mycelial solution, at 10-30% of the total medium volume, preferably at a concentration of [300 mg mycelia/100 ml] solution. Total medium volume is the sum of growth medium and mycelial solution. The hybrid sheet incubation 5 conditions are the same as for the bacterial incubation.

The mycelia grow with and onto the cellulose layer thereby forming a hybrid mycelial cellulose sheet. In an embodiment this hybrid formation occurs over a range of 10-20 days. In another embodiment, the hybrid sheet formation incubates until the sheet has a thickness of 3 mm. After incubation the hybrid sheet is harvested 6 as shown in FIGS. 1 and 2.

As shown in FIG. 1 the harvested hybrid mycelial cellulose sheets undergo treatment comprising chemical and physical processing. The processing steps are performed at atmospheric temperature and pressure. In a first processing, The HMC sheet is heated 7 in 100° C. water to remove remaining liquid medium. In a second processing, the HMC sheet is treated 8 with sodium hydroxide (0.1-0.5N) at 50° C. to improve sheet strength. The HMC sheet is then dried 9 to less than 15% moisture, preferably below 10% by methods generally available to experts in the field.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

What is claimed is:

1. A method for manufacturing a synthetic, leather-like hybrid mycelium cellulose sheet (HMCS), comprising:
   A) preparing a growth medium comprising molasses, ammonium dihydrogen phosphate, ammonium sulphate, acetic acid, water, and calcium carbonate;
   B) inoculating the growth medium with a cellulose producing bacteria (CPB), and incubating to produce a cellulose sheet (CS) of ≥10 mm thickness and at a pH≤3.6;
   C) inoculating the CS with a mycelium solution at 3 mg/mL concentration, and incubating to produce a HMCS of ≥3 mm thickness;
   D) heating the HMCS in 100° C. water;
   E) processing the HMCS with NaOH; and
   F) drying the HMCS.

2. The method of claim 1 wherein the cellulose producing bacteria is *Komagataeibacter xylinus*.

3. The method of claim 1, wherein the step B) incubation produces a CS of ≤40 mm thickness.

4. The method of claim 1, wherein the step B) incubation is between 5 and 15 days.

5. The method of claim 1 wherein the mycelium is *Ischnoderma resinosum*.

6. The method of claim 1, wherein the step C) incubation produces a HMCS of ≤5 mm thickness.

7. The method of claim 1, wherein the step C) incubation is between 10 and 20 days.

8. The method of claim 1 further comprising the step of drying said hybrid mycelial cellulose sheet to less than 15% moisture.

9. The method of claim 1, wherein the:
   A) molasses is at a concentration of ≥5 g/L;
   B) ammonium dihydrogen phosphate is at a concentration of ≥0.5 g/L;
   C) ammonium sulphate is at a concentration of ≥0.5 g/L; and
   D) acetic acid has a pH of ≥3.0; and
   E) calcium carbonate is at a concentration of ≥5 g/L.

10. A method for manufacturing a synthetic, leather-like hybrid mycelium cellulose sheet (HMCS), comprising:
    A) preparing a growth medium comprising molasses, ammonium dihydrogen phosphate, ammonium sulphate, acetic acid, water, and calcium carbonate;
    B) inoculating the growth medium with *Komagataeibacter xylinus*, to produce a cellulose sheet (CS) of ≥10 mm thickness and at a pH≤3.6;
    C) inoculating the CS with *Ischnoderma resinosum* solution at 3 mg/mL concentration, to produce a HMCS of ≥3 mm thickness;
    D) heating the HMCS in 100° C. water;
    E) processing the HMCS with NaOH; and
    F) drying the HMCS.

* * * * *